(12) United States Patent
Li et al.

(10) Patent No.: US 7,572,467 B2
(45) Date of Patent: Aug. 11, 2009

(54) **COMPOSITIONS COMPRISING ORGANIC EXTRACTS OF *GEUM JAPONICUM THUNB* VAR. AND THE USE THEREOF**

(75) Inventors: Ming Li, Hong Kong (CN); John Elsby Sanderson, Hong Kong (CN); Joseph Jao Yiu Sung, Hong Kong (CN); Kenneth Ka Ho Lee, Hong Kong (CN); Jack Chun Yiu Cheng, Hong Kong (CN); Edmund Cheung, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 10/496,333

(22) PCT Filed: Nov. 21, 2001

(86) PCT No.: PCT/CN01/01577

§ 371 (c)(1),
(2), (4) Date: Nov. 3, 2004

(87) PCT Pub. No.: WO03/043645

PCT Pub. Date: May 30, 2003

(65) Prior Publication Data

US 2005/0064048 A1    Mar. 24, 2005

(51) Int. Cl.
*A61K 36/00* (2006.01)
(52) U.S. Cl. .................................................. 424/725
(58) Field of Classification Search ................ 424/765; 514/783
See application file for complete search history.

(56) References Cited

FOREIGN PATENT DOCUMENTS

| CA | 2209222 A | * | 12/1998 |
| JP | 11199500 | | 7/1999 |
| JP | 11236334 | | 8/1999 |

OTHER PUBLICATIONS

McCutchenon, A. R. et al., Int. J. Pharmacogn (1997), 35(2): 77-83. Anti-mycobacterial Screening of British Columbian medicinal plants.*
Xu, X-X. et al., J. Nat. Prod. (1196), 59(7): 643-645. Anti-HIV triterpene acids from *Geum japonicum*.*
Dong, H et al., J. Nat. Prod. (1998), 61(11): 1356-60. Effects of tannins from *Geum japonicum* on the catalytic activity of thrombin and factor Xa of blood coagulation cascade.*
http://www.ibiblio.org.pfaf/cgi-bin/arr_html?Geum+japonicum (Apr. 12, 2005). Plants For A Future: Database Search Results.*
Ahuja, P et al. Physiological Reviews (2007); 87: 521-544. Cardiac myocyte cell cycle control in development, disease and regeneration.*
Arras, M. et al., "Monocyte activation in angiogenesis and collateral growth in the rabbit hindlimb," J. Clin. Invest. (1998) 101(1):40-50.
Arras, M. et al., "The delivery of angiogenic factors to the heart by microsphere therapy," Nat. Biotechnol. (1998) 16:159-162.
Banai, S. et al., "Effects of acidic fibroblast growth factor on normal and ischemic myocardium," Circ. Res. (1991) 69(1):76-85.
Choi, Y-H. et al., "Antioxidants in leaves of *Rosa rugosa*," Kor. J. Pharmacogn. (1997) 28(4):179-184.
Dong-Sheng, M. et al., "Research progress in chemical constituents and biological activities of *Geum* species," Acta Pharmac. Sinica (2000) 35(7):552-558.
Folkman, J., "Clinical applications of research on angiogenesis," New Eng. J. Med. (1995) 333(26):1757-1763.
Kurz, H. et al., "Automated evaluation of angiogenic effects mediated by VEGF and P1GF Homo- and Heterodimers," Microvasc. Res. (1998) 55:92-102.
Lazarous, D.F. et al., "Effects of chronic systemic administration of basic fibroblast growth factor on collateral develoment in the canine heart," Circulation (1995) 91(1):145-153.
Perry, L.M., Medicinal Plants of East and Southeast Asia: Attributed Properties and Uses, MIT Press, Cambridge, MA (1980) 343.
Pu, L.Q. et al., "Enhanced revascularization of the ischemic limb by angiogenic therapy," Circulation (1993) 88(1):208-215.
Risau, W., "Mechanisms of angiogenesis," Nature (1997) 386:671-674.
Schlaudraff, K. et al., "Growth of 'new' coronary vascular structures by angiogenetic growth factors," Eur. J. Cardiothorac. Surg. (1993) 7:637-643.

(Continued)

*Primary Examiner*—Michele C. Flood
(74) *Attorney, Agent, or Firm*—Michael Best & Friedrich LLP

(57) ABSTRACT

An organic extract of *Geum japonicum thunb* var. (EGJ), and a pharmaceutical composition comprising the same. The organic EGJ has been identified to show potent dual effects on stimulating early growth (less than 48 hours) of new vessels both in ischemic heart muscles and in infracted heart muscles, and on triggering myocardial regeneration in myocardial infarction, and therefore, may be used in the treatment of ischemic diseases in human being or animals including ischemic heart disease and ischemic limbs, and damaged myocardium associated diseases.

13 Claims, 2 Drawing Sheets

OTHER PUBLICATIONS

Uchida, Y. et al., "Angiogenic therapy of acute myocardial infarction by intrapericardial injection of basic fibroblast growth factor and heparin sulfate: an experimental study," Am. Heart J. (1995) 130:1182-1188.

Unger, E.F. et al., "Extracardiac to coronary anastomoses support regional left ventricular function in dogs," Am. J. Physiol. (1993) 264:H1567-1574.

Unger, E.F. et al., "A model to assess interventions to improve collateral blood flow: continuous admiistration of agents into the left coronary artery in dogs," Cardiovasc. Res. (1993) 27:785-791.

Ware, J.A., Angiogenesis & Cardiovascular Disease (J.A. Ware and M. Simons, eds.) Oxford University Press, New York, Oxford (1999) 30-59.

Xu, H-X. et al., "A new anti-HIV triterpene from *Geum japonicum*," Chem. Pharm. Bull. (2000) 48(9):1367-1369.

* cited by examiner

COMPOSITIONS COMPRISING ORGANIC EXTRACTS OF GEUM JAPONICUM THUNB VAR. AND THE USE THEREOF

FILED OF THE INVENTION

The invention is directed to a use of the extract of *Geum Japonicum thunb* var. (EGJ), particularly to a use of an organic EGJ in the treatment of ischemic diseases in human being or animals including ischemic heart disease and ischemic limbs, and diseases associated with damaged myocardium

BACKGROUND OF THE INVENTION

*Geum Japonicun Thunb* ver. is a plant generally growing in Jiangsu province, Jiangxi province, Guizhou province and Yunan province, China. *Geum* is a genus of 65 species of rhizomatous herbs and subshrubs with simple or pinnately lobed leaves and regular flowers such as *G. borisii, G. chiloense, G. coccineum, G. macrophyllum, G. montanum, G. reptans, G. rivale, G. triflorum, G. urbanum* and *G. japonicum* etc. *Geum japonicum Thunb.* is a perennial herb and the flowering plant of the Rosaceae family. Water extract of the whole plant of *Geum japonicum Thunb* has been used as a diuretic in traditional Chinese medicine, Perry, L. M., in Medicinal Plants of East and Southeast Asia, MIT Press, Cambridge, Mass., pp. 343 (1980). The plants of *Geum* species has been known to be rich in tannins. Several hydrolyzable tannins, such as gemin A, B, C, D, E and F, have been isolated from *Geum japonicum*, Dong, H., Chen, S. X., Kini, R. M., and Xu, H. X., *J. Nat. Products.* 61, 1356-60 (1998). In addition to tannins, some triterpenoids including 2-hydroxyoleanolic acid, 2-hydroxyursolic acid, 2,19-dihydroxy-ursolic acid, 2,3,19,23-tetrahydroxyurs-12-en-28-oic acid 28-O-D-glucopyranoside were isolated, Xu, H. X., Zeng, F. Q., Wan, M., and Sim, K. Y., *J. Nat. Products,* 59, 643-5 (1996).

However, no information has been disclosed on the use of an EGJ in treating ischemic diseases and damaged myocardium. Ischemic diseases, such as coronary heart disease remains the leading cause of death in the Western world, such as in America and in developed regions in Asia, such as in Hong Kong, and now becoming so in China as well, *American Heart Association,* 2001 *Heart and Stroke Statistical Update, Dallas, Tex.: American Heart Association,* 2000, 1-32. Currently, available therapeutic approaches thereto can only relieve symptoms and unfortunately, even with all the recent advances, cure of these kinds of ischemic diseases and damaged myocardium is difficult due to the lack of a method to grow functional new vessels at early stage in ischemic myocardium and the inability to regenerate cardiomyocytes, Uchida, Y., Yanagisawa-Miwa, A., Nakamura, F., Yamada, K., Tomaru, T., Kimura, K., and Morita, T., *Am Heart J.* 130: 1182-1188 (1995); Lazarous, D. F., Scheinowitz, M., Shou, M., Epstein, S. E., and et al, *Circulation* 91: 145-153 (1995); Pu, L. Q., Sniderman, A. D., Brassard, R., Lachapelle, K. J., Graham, A. M., Lisbona, R., and symes, J. F., *Circulation* 88: 208-215 (1993). According to previous studies in both acute and chronic ischemic animal models or clinical trials, angiogenesis by using growth factors, such as VEGF, aFGF, bFGF or PDGF requires time (on the order of 3-9 weeks) and is limited, (8-15) Risau, W., *Nature* 386: 671-674 (1997); Folkman, J., *N. Engl. J. Med.* 333: 1757-1763 (1995); Ware. J. A., *Anigiogeniesis and Cardiovascular Disease* (J. A. Ware and M. Simons, eds), Oxford University Press, New York, Oxford, 30-59 (1999); Ware, J. A., and Simons, M., *Nat. Med.* 3: 158-164 (1997); Arras, M., Ito, W. D., Scholz, D., Winkler, B., Schaper, J., and Schaper, W., *J. Clin. Invest.* 101: 40-50 (1998); Banai, S., Jaklitsch, M. T., Casscells, W., Shou, M., Shrivastav, S., Correa, R., Epstein, S. E. and Unger, E. F., *Circ. Res.* 69, 76-85 (1991); Arras, M., Mollnau, H., Strasser, R., Ito, W. D., Schaper, J., and Schaper, W., *Nat. Biotechnol.* 16: 159-162 (1998); Kurz, H., Wilting, J., Sandau, K., and Christ, B., *Microvasc. Res.* 55: 92-102 (1998), while myocardium necrosis due to coronary occlusion occurs very rapidly (hours), Unger, E. F., Shou, M., Sheffield, C. D., Hodge, E., Jaye, M., & Epstein, S. E., *Am. J. Phlysiol.* 264: H1567-1574 (1993); Unger, E. F., Banai, S., Shou, M., Jaklitsch, M., Hodge, E., Correa, R., Jaye, M., & Epstein, S. E., *Cardiovasc. Res.* 27: 785-791 (1993); and Schlaudraff, K., Schumacher, B., von Specht, B. U., Seitelberger, R., Schlosser, V., & Fasol, R., *Eur. J. Cardiothorac. Surg.* 7: 637-643 (1993). Therefore, therapeutic early angiogenesis and cardiomyogenesis may provide the most useful alternative strategy, which, if successful, may become the major therapeutic option in many ischemic diseases and damaged myocardium.

Up to now, there is no similar product available in the world market that is capable of inducing early angiogenesis in the heart and regeneration of myocardium is completely novel. According to previous studies in both acute and chronic ischemic animal models or clinical trials, some growth factors, such as VEGF, aFGF, bFGF or PDGF could enhance angiogenesis in certain degree, but it takes time (on the order of weeks) while myocardial necrosis due to coronary occlusion occurs very rapidly (in a mater of hours). Therefore, inducing early angiogenesis has become an important goal in reducing the size of infarction in the heart and rescuing affected tissue. Furthermore, even with all most recent advances in sciences and in research fields, there is no method or any drugs that could be used to regenerate cardiac myocytes.

In our recent studies, we have identified an extract of a Chinese herbal medicine-*geum Japonicum thunb* var that showed potent effects on stimulating early growth of new vessels (<48 h) and regeneration of cardiomyocytes in rabbit acute myocardium infraction model. In comparison to the period of weeks of naturally occurring angiogenesis and angiogenesis by using growth factors, EGJ induced angiogenesis in myocardium takes less than 48 hours. This unique feature of early angiogenesis induced by EGJ is therefore very useful in developing a new strategy for effective treatment of ischemic diseases, especially important in reduction of infarction size, rescuing affected cardiac myocytes while heart infarction occurs as demonstrated in our animal experiments.

The concept of therapeutic angiogenesis by augmenting the naturally occurring revascularizing process for the treatment of ischemic vascular diseases is a very attractive idea. It provides us with the opportunity to achieve more complete revascularization in patients with ischemic related diseases, such as coronary heart disease or heart infarction. For ischemic heart disease, apart from prevention, at present, blockages in the coronary arteries can only be relieved by surgery or angioplasty. There is no effective medicine that can stimulate the growth of new blood vessels (angiogenesis) at early stage. Furthermore, after myocardial infarction, the myocardium is incapable of regenerating new cardiomyocytes to replace the lost muscle cells. Scar tissues, which replace the necrosed myocardium, further, cause deterioration in cardiac function. Therefore, it is clear that an alternative revascularization strategy is required to treat ischaemia and stimulate replacement of damaged or lost heart muscle cells. Therapeutic angiogenesis and cardiomyogenesis would be the most useful alternative strategy, which may become the main therapeutic option in the treatment of many ischemic diseases including coronary heart diseases and ischemic limbs, and damaged myocardium. It may even be able to replace some of the current therapeutic modalities with a less invasive strategy, yet much more effective if early angiogenesis can be achieved.

The invention is to fulfill the purpose of growing new vessels at early stage and regenerating cardiac myocytes in infarcted myocardium to replace the damaged myocardium with the use of EGJ. EGJ can be applied by local myocardium injection directly to the distal parts of an occluded vessel in ischemic heart, or limbs. It can also be potentially developed into an oral administration (pills) or injection to blood stream or muscles in the patients who are unbearable to local myocardium injection and proved with no neoplasm formation or tumors.

The current invention relates to an organic extract, particularly a methanol extract of Geum Japonicum thunb var. that stimulates early angiogenesis and myocardial regeneration in ischemic heart and myocardial infarction and therefore is useful in treating ischemic diseases, such as ischemic heart disease including coronary heart disease, heart infarction, ischemic limbs, damaged myocardium and tissue healing.

SUMMARY OF THE INVENTION

An object of the invention is directed to a pharmaceutical composition comprising an organic EGJ for treating diseases in association with ischemia, tissue damage and tissue healing from which patients are suffering. The pharmaceutical composition according to the invention comprises an effective amount of the EGJ and a pharmaceutically acceptable carrier.

Another object of the invention is to provide a use of the organic EGJ for manufacturing a pharmaceutical for treating diseases in association with ischemia, tissue damage and tissue healing in a subject including human being, comprising mixing an effective amount of the organic EGJ with a pharmaceutically acceptable carrier or with other therapeutic reagent, such as Bone Morphogenetic Proteins for the treatment of bone defects and diseases.

Further object of the invention is to provide a method for preparing an extract from Geum Japonicum thunb var. by an organic solvent for treating diseases in association with ischemia, tissue damage and tissue healing in the subject. The method comprises breaking up the plant into pieces; soaking said pieces with an organic solvent; filtering the resultants; and evaporating the filter to dry.

Still object of the invention to provide a method for treating diseases in association with ischemia, tissue damage and tissue healing in a subject comprising administering to the subject a therapeutically effective amount of the organic EGJ.

BRIEF DESCRIPTION OF THE INVENTION

DETAILED DESCRIPTION OF THE INVENTION

Figure 1:
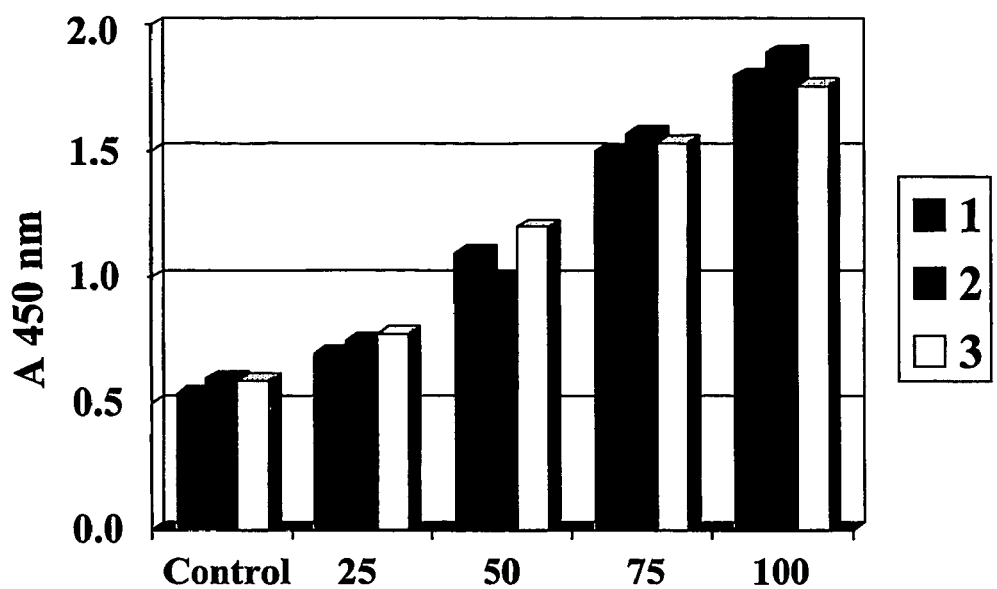
FIG. 1 shows that an EGJ according to the invention enhances the proliferation of HVEC in culture with different doses.

In the process for preparing an extract from a plant Geum Japonicum thunb var. by an organic solvent, the dried plant is preferably used. In that case, the plant is preferably broken up as powder.

The abbrevation "EGJ" used in the invention, without specific indication, means an extract of the plant Geum Japonicum thunb var. by an organic solvent discribed below.

Organic solvents used in the process of the invention are in a state of liquid at 25°, and may be selected form the group consisting of aliphatic hydrocarbons or aromatic hydrocarbons, ketones (aldehydes), carboxylic acids, esters, and ethers, which are not substituted or substituted with one or more substituent(s), or a mixture thereof.

The term "aliphatic hydrocarbon(s)" used herein means an alkane, an alkene, an alkyne and an alicyclic hydrocarbon, and in general includes 4-20 carbons.

The term "substituent(s)" is selected from the group consisting of halo, hydroxy, alkyl, alkenyl, alkynyl, alkoxyl, alkylthio, alkenoxyl, alkenylthio, alkynoxyl, and alkynylthio. Of the substitutes, lower alkyl, lower alkenyl, lower alkynyl, lower alkoxyl, lower alkylthio, lower alkenoxyl, lower alkenylthio, lower alkynoxyl, and lower alkynylthio are preferable. The number of the substituents may be from 1 to 3.

The term "alkyl" refers to a saturated aliphatic hydrocarbon including straight chain and branched chain groups. Preferably, the alkyl group has 1 to 20 carbon atoms (whenever numerical range; e.g. "1-20" is used herein, it means that the group referred to, in this case the alkyl group, may consist of 1 carbon atom, 2 carbon atoms, 3 carbon atoms, etc. up to and including 20 carbon atoms).

The term "lower alkyl, lower alkenyl, lower alkynyl, lower alkoxyl, lower alkylthio, lower alkenoxyl, lower alkenylthio, lower alkynoxyl, or lower alkynylthio" used in the invention contains 1-6 carbons.

Among the substituted aromatic hydrocarbons, those substituted by chlorine and lower alkyl such as chlorobenzene, toluene and xylene are preferable.

Among the solvents of the invention, alcohols, ethers, ketones, carboxylic acids and esters thereof containing 2-18 carbon atoms are preferably. Of these solvents, lower alkyl alcohols are preferably, more preferably are $C_{1-4}$ alochols and most preferably is methanol.

The step of soaking in the invention may be conducted at a temperature between 10° and 100°. It depends on the boiling point of a solvent to be used. In general, the step may be conducted at a temperature between 10° and the boiling point of the solvent. Preferably, this step is undertaken at an ambient temperature.

In the pharmaceutical composition of the invention, the term of "effective amount" or "therapeutically effective amount" is obvious for those skilled in the art. It depends on age, weight, and condition of the subject to be treated, and the manner to be administrated. In general, the extract in the composition varies from 0.01% to 99.99%, preferably from 1% to 99%, more preferably from 10% to 90%, and most preferably from 30% to 70%, by weight.

A "patient" or "subject" used herein means a human or an animal. In general, it implies an animal or a human. The animal may be a domestic animal or game animal such as cows, horses, pigs, deer, rabbits, dogs and others suffering from the diseases mentioned herein.

An "active component" mentioned in the invention means an EGJ by an organic solvent disclosed in the present invention.

A "carrier" or "pharmaceutically acceptable carrier" used herein means a component or an ingredient that is acceptable in the sense of being compatible with other ingredients of the pharmaceutical composition as disclosed herein and not overly deleterious to the patient to which the composition is administered, including any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Since the active component of the composition of the invention is lipid soluble, when the compositions are formed as liquid formulations, the active component is first dissolved in those carriers including a $C_{2-12}$ alcohol such as ethanol, n-propanol, i-propanol, n-butanol, and benzyl alcohol, glycerol, propylene glycol, N,N-dimethylacetamide, DMSO, olive oil, cottonseed oil, peanut oil, poppyseed oil, sesame oil, soybean oil and other vegetable oil, and then, if necessary, prepared as desired formulations. The carrier may also comprise a solid selected from those conventionally used in the pharmaceutical formulation art, such as gelatine, lactose, magnesium stearate, talc, calcium carbonate, magnesium carbonate, starch (corn starch and potato starch) and those well known in the prior art.

The pharmaceutical composition may also comprise one or more components typically used in the pharmaceutical formulation art such as surfactants, propellants, flavoring agents, preservatives, buffers, fillers, binders, disintegrants, lubricants and the like, which can be determined by those skilled in the art according to the formulations to be prepared.

Pharmaceutical compositions used in the present invention include systemic and topical formulations and among these preferred are formulations which are suitable for inhalation, oral, rectal, vaginal, intracavitary, intraorgan, topical including buccal, sublingual, dernal and intraocular, parenteral including subcutaeous, intradermal, intramuscular, intravenous and intraarticular, and transdermal administration.

The compositions may be presented in single or multiple unit dosage forms as well as in bulk, and may be prepared by any of the methods well known in the art of pharmacy. All the methods include the step of bringing the active component, EGJ, into association with a carrier which constitutes one or more accessory ingredients. The formulations are generally prepared by uniformly and intimately bringing the active compound into association with a liquid carrier, a finely divided solid carrier, or both, and then, if necessary, shaping the product into desired formulations.

Compositions suitable for oral administration may be presented in discrete units, such as capsules, cachets, lozenges, or tablets, each containing a predetermined amount of the active component; as a powder or granules; as a solution or a suspension in an aqueous liquid; or as an oil-in-water or water-in-oil emulsion. Composition for oral administration may optionally include enteric coatings known in the art to prevent degradation of the compositions in the stomach and provide release of the active component in the small intestine. Compositions suitable for buccal administration include lozenges comprising the active component in a flavored base, usually sucrose and acacia or tragacanth; and pastilles comprising the active component in an inert base such as gelation and glycerin or sucrose and acacia.

Compositions suitable for parenteral administration comprise sterile aqueous and non-aqueous injection solutions of the active component, whose preparations are preferably isotonic with the blood of the intended recipient. These preparations may contain antioxidants, buffers, bacteriostats and solutes which render the compositions isotonic wit the blood of the intended recipient. Aqueous and non-aqueous sterile suspensions may contain suspending agents and thickening agents. The compositions may be presented in unit-dose or multi-dose containers such as sealed ampoules and vials, and may be stored in a sterile liquid carrier such as a saline or water-for injection immediately prior to use. Extemporaneous injection solutions and suspensions may be prepared from sterile powders, granules and tablets.

Compositions according to the invention suitable for topical application to the skin preferably take the forms of an ointment, cream, lotion, paste, gel, spray, aerosol, or oil. Compositions suitable for transdermal administration may be presented as discrete patches adapted to remain in intimate contact with the epidermis of the recipient for a prolonged period of tome. Compositions for suitable for transdemal administration may also-be delivered by iontophoresis, and typically take the form of an optionally buffered aqueous solution of the active component.

The active component is preferably formulated in dosage unit form for ease of administration and uniformity of dosage. "Dosage unit form" as used herein refers to a physically discrete unit of the pharmaceutical composition appropriate for the patient to be treated. Each dosage should contain the quantity of the active component calculated to produce the desired therapeutic effect either as such, or in association with the selected pharmaceutical carrier. Typically, the active component will be administered in dosage units containing from about 0.1 mg to about 500 mg by weight in the composition, with a range of about 1 mg to about 100 mg being preferred.

The active component of the invention may be administered at dosage levels of about 0.001 to about 120 mg/kg of subject body weight per day and preferably from about 0.01 to about 30 mg/kg of subject body weight per day, one or more times a day, to obtain the desired therapeutic effect.

By way of example, a suitable dose for oral administration would be on the order of 30 mg/kg of body weight per day, whereas a typical dose for intravenous administration would be on the order of 1-10 mg/kg of body weight per day.

The pharmaceutical composition according to the invention may be used to treating the diseases associated with ischemia such as ischemic heart disease and ischemic limbs, tissue damage, such as soft or hard tissue damage, operation cut and tissue healing that requires neovascularization, such as femur head (neck) fracture or lower ⅓ tibia fracture.

For the treatment of skeletal muscle injury, skin injuries, operation cut and other soft tissue injuries, formations for topical administration is preferable. However, pastes, ointments or powders are preferably formulations for those through external administrations such as burn. For the treatment of heart disorders, it is recommend that local injection with solutions be used, so that the local concentration of the drug would be high and function better and more effective. However, if the patient simultaneously suffers from tumor or malignant neoplasm, it is not recommend that systemic injection or oral administration be performed, and local injection should be a safer way.

In the process for manufacturing a pharmaceutical composition by an EGJ for treating diseases associated with ischemia, tissue damage and tissue healing according to the invention, an effective amount of EGJ is mixed with one or more carriers indicated above. In the pharmaceutical composition, the EGJ usually is of from 0.01% to 99.99% by weight. Preferably, the EGJ is of 1-99% by weight in the composition.

EXAMPLES

During the course of screening for angiogenic reagents from Chinese medicine, the methanol extract of *Geum japonicum thunb* var. has been identified that showed potent dual effects on stimulating early growth (less than 48 hours) of new vessels both in ischemic heart muscles and in infarcted heart muscles, and on triggering myocardial regeneration in myocardial infarction.

Example 1

1 kg of dried whole plant of *Geum japonicuin thunb* var collected from Guizhou Province of China was powdered. The powder of the plant was then soaked with methanol (8 L) at room temperature for 2-3 hours. Resultants were filtered and the filter was evaporated to dry under a vacuum (50° C.) to yield a powder (50 g).

An analysis by chromatography and NMR showed that EGJ contains mainly tannins, triterpenes including 2-alpha, 19-alpha-dihydroxy-3-oxo-12-ursen-28-oic acid, ursolic acid, epimolic acid, maslinic acid, euscaphic acid, tormentic acid, 28-beta-D-glucoside of tormentic acid and etc.

Example 2

EGJ powder obtained in Example 1 0.4 g
5% DMSO water solution 100 ml
EGJ powder was dissolved in 100 ml 5% DMSO water solution to obtain a working solution.

Example 3

EGJ of Example 1 0.1 g
Corn starch 0.5 g
Lactose 1.87 g
Magnesium stearate 0.03 g EGJ powder of example 1, corn starch and lactose were uniformly mixed. To the mixture a little water was added. Resulting materials was filtered and dried. Magnesium stearate was added to the mixture and uniformly mixed. The resultant was pelleted by a pelletizer. Each pellet weighs 250 mg and comprises 10 mg of active component.

Example 4

EGJ of Example 1 80 mg
Sodium Chloride 8 mg
EDTA 1 mg
Buffer (pH6.5) of sodium phosphate 10 mg
Polyethylene glycol ether 10 mg
Distilled Water added to 2 ml All the components were dissolved in distilled water then to the mixture distilled water was added to 2 ml. Resultant solution was filtered with a sterile filter to formulate a nasal inhalation.

Experiment 1

An EGJ solution in 5% DMSO (Example 2) was tested for its specific angiogenic and myogenic activities to stimulate proliferation of cultured human vascular endothelial cells (HVEC) and myogenic cells (C2C12), as shown in FIG. 1. In FIG. 1, reference numerals 1, 2, and 3 respectively indicate different culture plates in the same condition. It is shown that EGJ could significantly enhance the proliferation of HVEC in culture in a dose dependent manner compared with 5% DMSO control. It was also demonstrated that this EGJ solution showed potent dual effects on both angiogenesis and myogenesis in infarcted myocardium according to our animal experiments. In chromatography determination, the EGJ was solubilized in solvent and applied on a column of Sephadex LH-20 equilibrated with 10% Methanol and eluted with gradient $H_2O$-Methanol (increasing amount of Methanol). 12 fractions were eluted and tested for their dual activities in enhancing the proliferation of cultured HVEC and C2C12 cells. This methanol extract (EGJ) with the specific dual activities was further tested in subsequent in vivo experiments. NMR was used to determine the identities of the compounds contained in the active fraction.

Experiment 2

This EGJ dissolved in 5% DMSO was further investigated in rabbit heart infarction model to investigate its effects on heart muscles. The reason for choosing the rabbit as heart infarction model is that rabbits have end-arteries without arteriolar connections so that acute coronary artery occlusion could lead to rapid transmural infarction. The left circumflex (LCX) or left anterior descending artery (LAD) of the experimental animals was ligated respectively. Directly after ligation, a single injection of EGJ (a saturated solution of ECJ in 5% DMSO, 0.5 ml) or control solution (5% DMSO) was applied at the distal ends of the ligated arteries respectively. On day 4 or on day 7 after ligation, the animals were sacrificed and the hearts were removed for histological studies.

Figure 2:
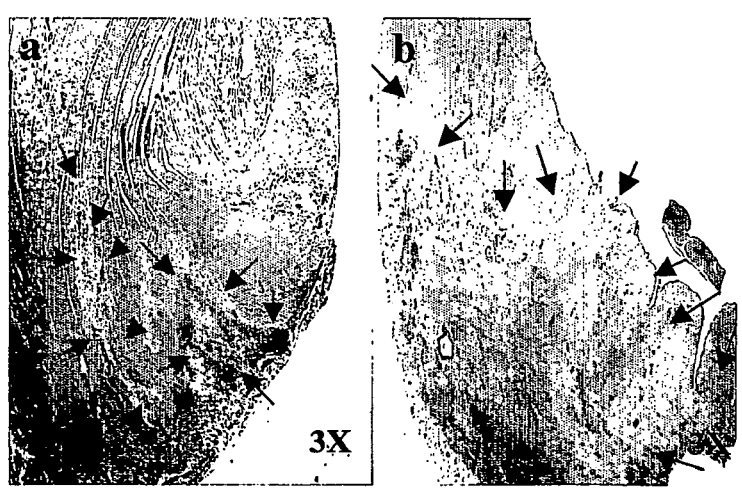
FIG. 2 shows the size of heart infarction area of a rabbit after treated with an EGJ according to the invention.
Figure 3:
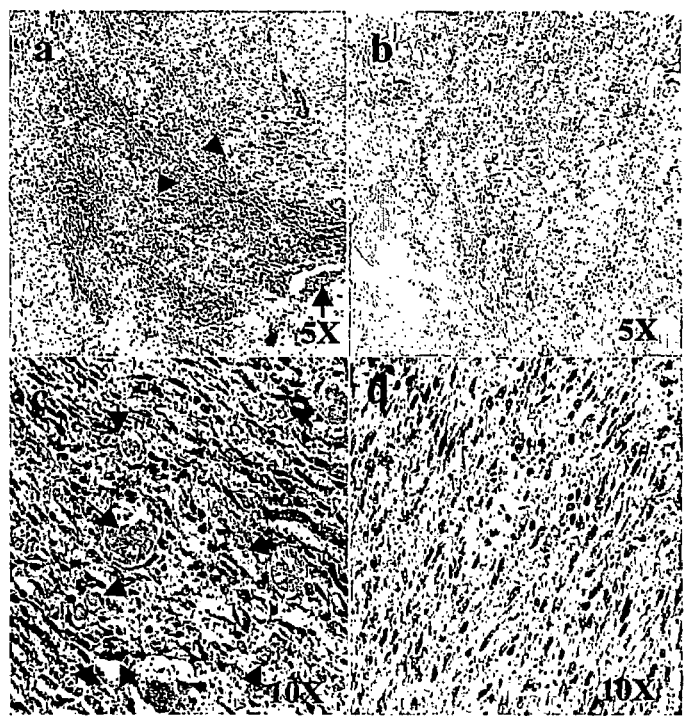
FIG. 3 shows that new blood vessels filled with blood cells are formed within the infarction area of a rabbit after treated with an EGJ according to the invention.

FIG. 2 showed that the size of infarction area was 3-5 times smaller in EGJ treated animals (a) as indicated by blue arrows than that in the control (b). It was shown in FIG. 3 that many newly formed blood vessels filled with blood cells were observed in myocardium infarction segments (a & c) as indicated by blue arrows in EGJ treated animals. In contrast, much less vessels were observed in the control (b & d).

Figure 4:
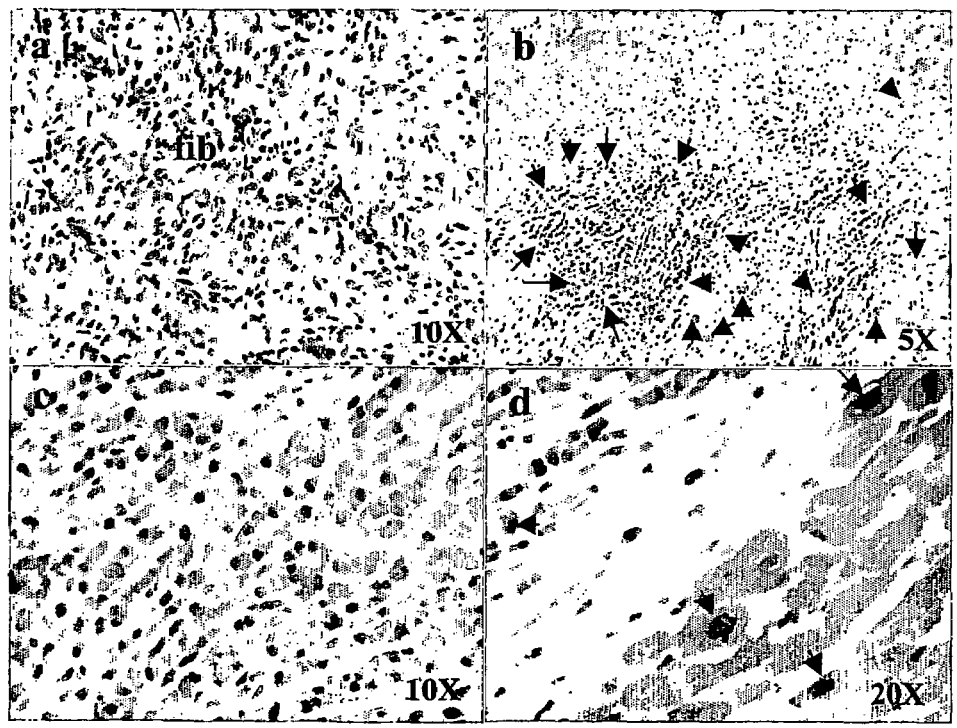
FIG. 4 shows that PCNA-positively stained cardiomyocytes in the infarction area are newly regenerated, and especially the PCNA positively stained cell clusters in the central zone of the infarction are most significant after treated with EGJ according to the invention.

On day 7, numerous newly regenerated cardiomyocytes with PCNA-positively stained nuclei were found around infarction borders, with some organized as clusters inside the infarction area of ECJ treated hearts, and numerous vessles were also found as indicated by black arrows, as shown in FIG. 4, (b). In contrast, there were only a few PCNA positively stained newly regenerated cardiomyocytes found along the borders of the infarction and there were no central clustered newly regenerated cardiomyocyte found in control heart, and it was mainly fibroblast that occupied the infarction area, as shown in FIG. 4, (a). The sections were further immunohistochemically stained with mono-clonal myosin heavy chain (MF20) antibodies to confirm the PCNA positively stained nuclei were cardiomyocytes. In FIG. 4, (c) is the high power field of the blue arrow surrounded area in (b), and in (d), some newly regenerated cardiomyocyte were also found around infarction edges of EGJ treated hearts as indicated by blue arrows.

By using immunohistochemical staining with monoclonal antibodies against PCNA, only the newly regenerated nuclei of cells could be positively stained. By using anti-MF20 immunohistochemical staining procedure, only cardiomyocytes could be positively stained. Combining these double immunohistochemical staining procedures and morphological analysis, the newly regenerated cardiomyocytes could be reliably identified. The nuclei of intact undamaged cardiomyocytes surrounding the infarction area were negatively stained for PCNA but the cytoplasm was positively stained for MF20 (brown stained cells).

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

We claim:

1. A method for stimulating angiogenesis or myocardial regeneration in a subject having an ischemic heart disease or a myocardial infarction, comprising administrating to said subject an amount of an organic solvent extract of *Geum japonicum thunb* var. effective to stimulate angiogenesis or myocardial regeneration.

2. The method of claim 1, wherein the extract of *Geum japonicum thunb* var. is administered within 48 hours of the myocardial infarction.

3. The method of claim 1, wherein the amount of the extract of *Geum japonicum thunb* var. administered has a therapeutic effect.

4. The method of claim 1, wherein the extract of *Geum japonicum thunb* var. is administered in an amount ranging from about 0.001 mg to about 120 mg of the extract per kilogram of subject body weight per day.

5. The method of claim 4, wherein the extract of *Geum japonicum thunb* var. is administered in dosage unit form.

6. The method of claim 1, wherein the extract of *Geum japonicum thunb* var. is administered in a dosage unit form including a pharmaceutically acceptable carrier.

7. The method of claim 1, wherein the extract of *Geum japonicum thunb* var. stimulates regeneration of cardiomyocytes.

8. The method of claim 1, wherein the extract of *Geum japonicum thunb* var. reduces in size the area of the myocardial infarction area 3-5 times as compared to a subject not treated with an extract of *Geum japonicum thunb* var. as measured by comparison of newly formed blood vessels.

9. The method of claim 1, wherein the extract of *Geum japonicum thunb* var. is administered orally.

10. The method of claim 1, wherein the extract of *Geum japonicum thunb* var. is injected locally.

11. The method of claim 1, wherein the solvent is a lower alkyl alcohol.

12. The method of claim 11, wherein the solvent is a lower alkyl alcohol having 1-6 carbons atoms.

13. The method of claim 11, wherein the solvent is methanol.

* * * * *